United States Patent [19]

Laco

[11] Patent Number: 5,669,671
[45] Date of Patent: Sep. 23, 1997

[54] SUPPORT HARNESS FOR A PERSON SEATED IN A CHAIR

[76] Inventor: Randall J. Laco, 703 Ninth St., Suite 201, Durham, N.C. 27705

[21] Appl. No.: 669,036

[22] Filed: Jun. 24, 1996

Related U.S. Application Data

[63] Continuation-in-part of Ser. No. 235,480, Apr. 29, 1994, Pat. No. 5,529,383.

[51] Int. Cl.⁶ ................................................ A62B 35/00
[52] U.S. Cl. ............................................. 297/485; 297/468
[58] Field of Search .................................. 297/468, 485, 297/464; 24/573.1, 633; 128/869, 870, 876

[56] References Cited

U.S. PATENT DOCUMENTS

| | | |
|---|---|---|
| 579,818 | 3/1897 | Cooley. |
| 1,316,163 | 9/1919 | Kennedy ............................ 297/485 X |
| 2,437,585 | 3/1948 | Zimmern ............................ 297/468 |
| 2,689,604 | 9/1954 | Hourruitiner ....................... 297/485 |
| 2,741,412 | 4/1956 | Hinkle. |
| 2,814,336 | 11/1957 | Manhart et al. .................... 297/468 |
| 3,174,798 | 3/1965 | Sprague ............................. 297/485 |
| 3,957,304 | 5/1976 | Koutsky et al.. |
| 4,015,878 | 4/1977 | Perkins. |
| 4,093,307 | 6/1978 | McLennan. |
| 4,177,807 | 12/1979 | Ocel et al.. |
| 4,634,184 | 1/1987 | Hitson. |
| 4,706,992 | 11/1987 | Downing et al.. |
| 4,901,407 | 2/1990 | Pandoler et al. ..................... 24/633 |
| 5,148,563 | 9/1992 | Klearman et al.. |

*Primary Examiner*—Peter R. Brown
*Attorney, Agent, or Firm*—Terrance L. Siemens

[57] ABSTRACT

A harness for maintaining erect posture of a person seated in a chair. The harness includes an anchoring strap which encircles the seatback of the chair and a supporting strap which encircles the torso of the person seated in the chair. The supporting strap comprises two separate straps fastened respectively at the right and left sides of the anchoring strap. The two straps meet in front of the seated person and are buckled together. Apart from the buckle, all straps are secured in their operative locations by frictional engagement, thereby avoiding rivets, stitching, buttons, snaps, or other fasteners which penetrate or otherwise disturb the snaps. Optionally, the constituent straps of the supporting strap have elastic sections, for resistably yielding to the person when the person inclines his or her torso. Also optional is a cushioned cover for covering the buckle, to avoid discomfort to the seated person.

7 Claims, 2 Drawing Sheets

5,669,671

SUPPORT HARNESS FOR A PERSON SEATED IN A CHAIR

REFERENCE TO RELATED APPLICATION

This application is a Continuation-In-Part of Ser. No. 08/235,480, filed Apr. 29, 1994 now U.S. Pat. No. 5,529,383.

BACKGROUND OF THE INVENTION

1. FIELD OF THE INVENTION

The present invention relates to a harness for supporting a person in a seated position in a chair having a seat and a seatback. More particularly, the harness includes a first strap engaging the chair seatback by encirclement thereof and a second strap passing in front of and supporting the person seated in the chair. The harness includes fasteners connecting the first strap to the second strap, apparatus for adjusting length of the two straps, and a clasp for closing the second strap around the seated person.

2. DESCRIPTION OF THE PRIOR ART

Persons who must sit in chairs for protracted periods of time, such as those who work at desks, are subject to becoming uncomfortable in a seated position. They may attempt to relieve discomfort by slouching or otherwise altering their posture. While change of posture may provide temporary relief to muscles which are given an opportunity to relax or flex, this approach may lead to aggravating the original condition by maintaining posture which becomes unnatural or uncomfortable as time passes. The situation may result in protracted stress and discomfort which may lead to chronic afflictions further resulting in loss of performance at work. The workers may engage in reduced efficiency when working, may become quick to fatigue, may display irritability, and may engage in absenteeism from work.

The prior art has suggested apparatus intended to be attached to a pre-existing chair, for maintaining a person to be held erect in or tethered to the chair.

An example is found in U.S. Pat. No. 579,818, issued to Ella I. Cooley on Mar. 30, 1897, wherein a safety belt is described. Cooley's safety belt comprises two separate loops connected to one another. The purpose of Cooley's belt is to secure a child in a chair. Three buckles must be fastened to accomplish this. By contrast, the present invention has but one buckle, employing sliding fasteners instead of buckles at other fastening points. Also, the present invention lacks a separate strap connecting two separate loops, as provided by Cooley. Instead, the user is partially encircled by two straps projecting from the loop which engages the chair, which two straps mutually fasten by a buckle. In a further departure from Cooley, members encircling the user have elastic portions for resilient stretching. By contrast, Cooley tethers two inelastic loops together by an elastic tether.

In U.S. Pat. No. 2,689,604, issued to Ramon Hourruitiner on Sep. 21, 1954, a safety belt for automobiles is shown. An anchoring member encircles a vehicle seatback, and a second member for encircling a user projects from the first member. Unlike the present invention, the anchoring member has a buckle including a pin for penetrating a hole formed in the fabric of the first member. Holes and pins are absent in an equivalent fastener in the present invention, being supplanted by a sliding fastener. Hourruitiner's device also lacks adjustability of length of the member encircling the user. By contrast, the present invention enables length adjustment of an equivalent encircling member. Attachment of the encircling member to the anchoring member is enabled by hooked clasp in Hourruitiner. By contrast, the present invention employs slotted slide fasteners in corresponding locations. Slotted fasteners require that a strap be passed through several slots. Attachment of a clasp to one strap and a ring to a second strap, as required by Hourruitiner, are unnecessary in the present invention. Hourruitiner provides elasticity along the entirety of the member encircling the user. By contrast, the present invention provides a limited section of an equivalent member to be elastic.

U.S. Pat. No. 2,741,412, issued to Noel C. Hinkle on Apr. 10, 1956, describes a safety belt comprising two loops joined to one another at three points. At a point where both loops touch one another, a third member encircles both loops, securing the latter together. Also, the two loops are joined by two tethers, each tether forming a tangent to both loops. Both loops are fastened by snap hook fasteners. By contrast, the present invention lacks two separate loops. Also, fasteners closing the anchoring loop also assist in length adjustment. Hinkle's device separates these functions, and hence requires additional structure to achieve the two functions.

U.S. Pat. No. 4,706,992, issued to Deborah L. Downing et al. on Nov. 17, 1987, describes an auxiliary seat belt for attachment to a pre-existing seat belt of a motor vehicle. This device lacks an anchoring loop for engaging a seat, as found in the present invention, as well as lacking construction wherein the user encircling member projects from the anchoring member, as seen in the present invention.

None of the above inventions and patents, taken either singly or in combination, is seen to describe the instant invention as claimed.

SUMMARY OF THE INVENTION

The present invention provides a harness for supporting a person seated in a chair in an erect posture. The harness is intended for use with chairs having a cushioned seatback. The harness comprises an anchoring loop encircling the seatback, and a supporting strap which is fastened about the user's torso. The anchoring loop adjusts to the circumference and configuration of the seatback, so that the novel harness may be employed with most pre-existing chairs.

Three straps are employed in the novel harness. One is the anchoring member. The other two straps form the member encircling the seated person. A buckle is fastened to the end of one of these other two straps. Apart from attachment of the buckle, no connectors or fasteners need be fastened to a strap. Nor is any strap stitched or otherwise permanently fastened to itself to form a loop. The present invention thus avoids complicated construction and cutting, stitching, or perforating of the straps.

Most connections, where required, are secured by sliding clips which slip over a strap and secure it by friction when drawn tight. Thus, most components other than straps are monolithic, and may be fabricated from a molding process, or other process requiring only one step.

An exception to connection by sliding clips is seen where the body encircling straps attach to the anchoring strap. Here, a snap hook engages a ring. This combination enables universal flexing, so that the body encircling straps may conform to torso inclination. If not free to pivot to conform to torso inclination, the body encircling straps could possibly cause discomfort to the user.

Reliance upon sliding clips for fastening has advantages beyond uncomplicated fabrication. The invention is easily fastened both to a chair and around the person seated in the chair. Fastening is secure yet readily adjustable. Because the various straps are generally unencumbered by rivets, holes, and other structure, they are readily adjusted for length, and especially to assure that components are located where desired.

For example, the novel harness is most comfortable when straps encircling the user attach to the anchoring strap precisely at the right and left sides of the anchoring strap. If they attached more towards the front, they would interfere with the user's comfort by interposing themselves between the user's back and the seatback. If located more to the rear of the anchoring strap, they would exhibit a greater tendency to pull responsive to torso movement, and would lose universal flexure provided by the hook and ring fasteners. In a second example, the body encircling straps may be precisely adjusted to assure that the buckle be located at the front and center of the user's torso. If not centered, the buckle would possibly cause an uncomfortable distraction.

Sliding clips enable ready mounting of the invention on a chair. The buckle, which is preferably a cam buckle requiring only opening and closing, and no manipulation of small parts, enables rapid fastening of the encircling straps about the torso of the person seated in the chair. Therefore, the invention is quickly and easily installed on a chair, and may be left there. When the user wishes to don the harness, minimal effort is required, that being limited to closing the buckle over the free end of the remaining encircling strap.

A padded cover is optionally provided to cushion the buckle, so that the buckle will be less intrusive or discernible to the user.

The straps encircling the seated person have sections of elastic material. These sections allow some limited stretching to accommodate the seated person when inclining his or her torso.

Accordingly, it is a principal object of the invention to provide a harness suitable for maintaining a seated person in an erect posture in a chair having a broad seatback and not originally provided with such a harness.

It is another object of the invention to avoid complicated and cumbersome construction.

It is a further object of the invention to enable rapid installation of the invention on a chair and minimal effort in donning the invention.

Still another object of the invention is to avoid cutting, perforating, or permanently attaching apparatus to the various straps to the greatest feasible degree.

An additional object of the invention is to provide elasticity of the encircling straps, for accommodating inclination of the torso.

It is again an object of the invention to cushion the buckle, to render it less obtrusive than would otherwise be the case.

Yet another object of the invention is to provide universal flexure of the torso encircling straps where they attach to the anchoring strap.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
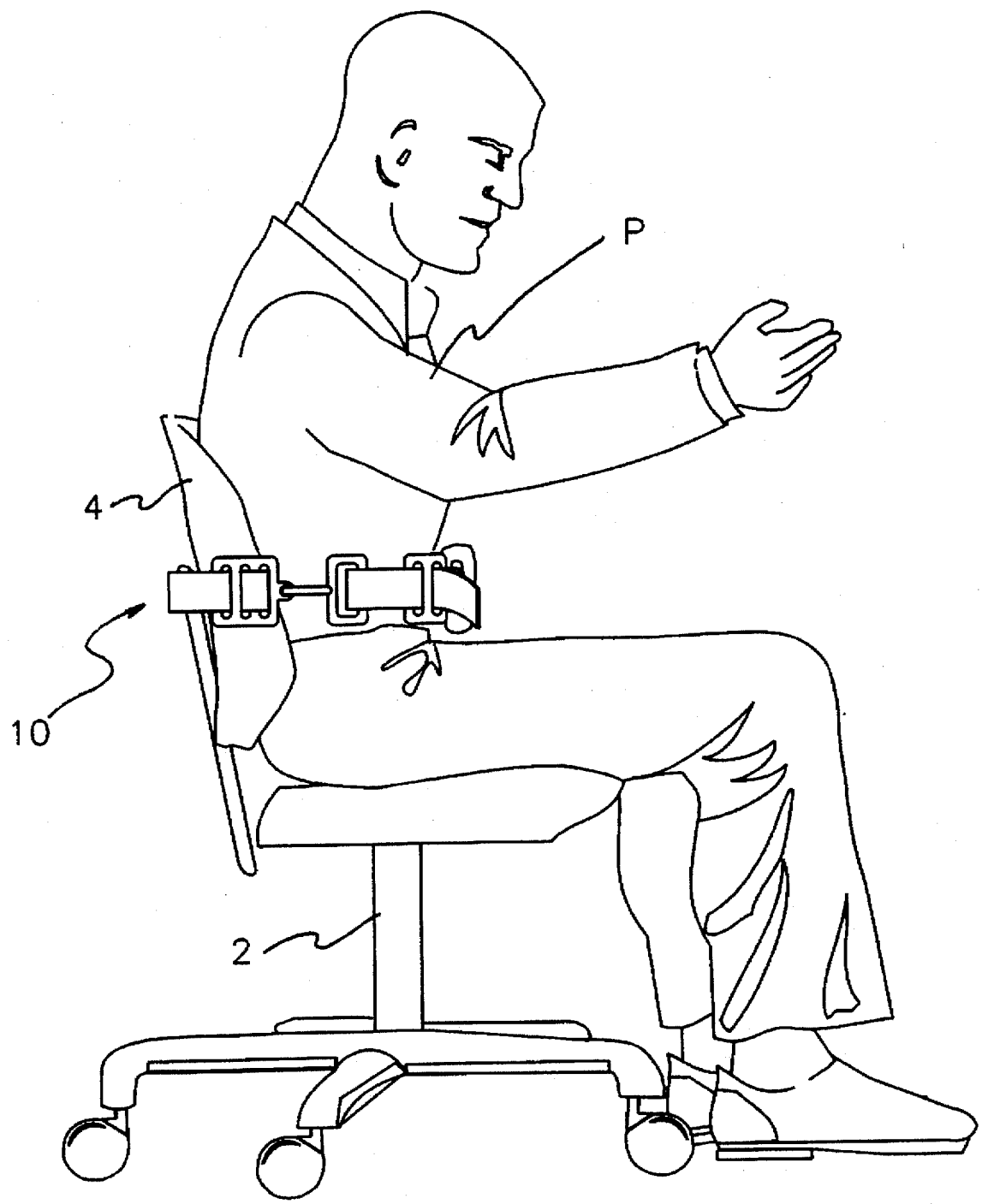
FIG. 1 is an environmental, side elevational view of the invention.

Turning now to FIG. 1 of the drawings, the novel harness 10 is shown maintaining a person P seated in a chair 2 in an erect posture. Harness 10 is intended for use with a chair which has a broad, cushioned seatback 4. Such chairs have little solid or rigid structure enabling effective attachment of a posture aid, and thus harness 10 must securely engage chair 2 while not unduly discomforting the person P seated in chair 2. Harness 10 must also adjust to cooperate with seatbacks of different dimensions.

Figure 2:
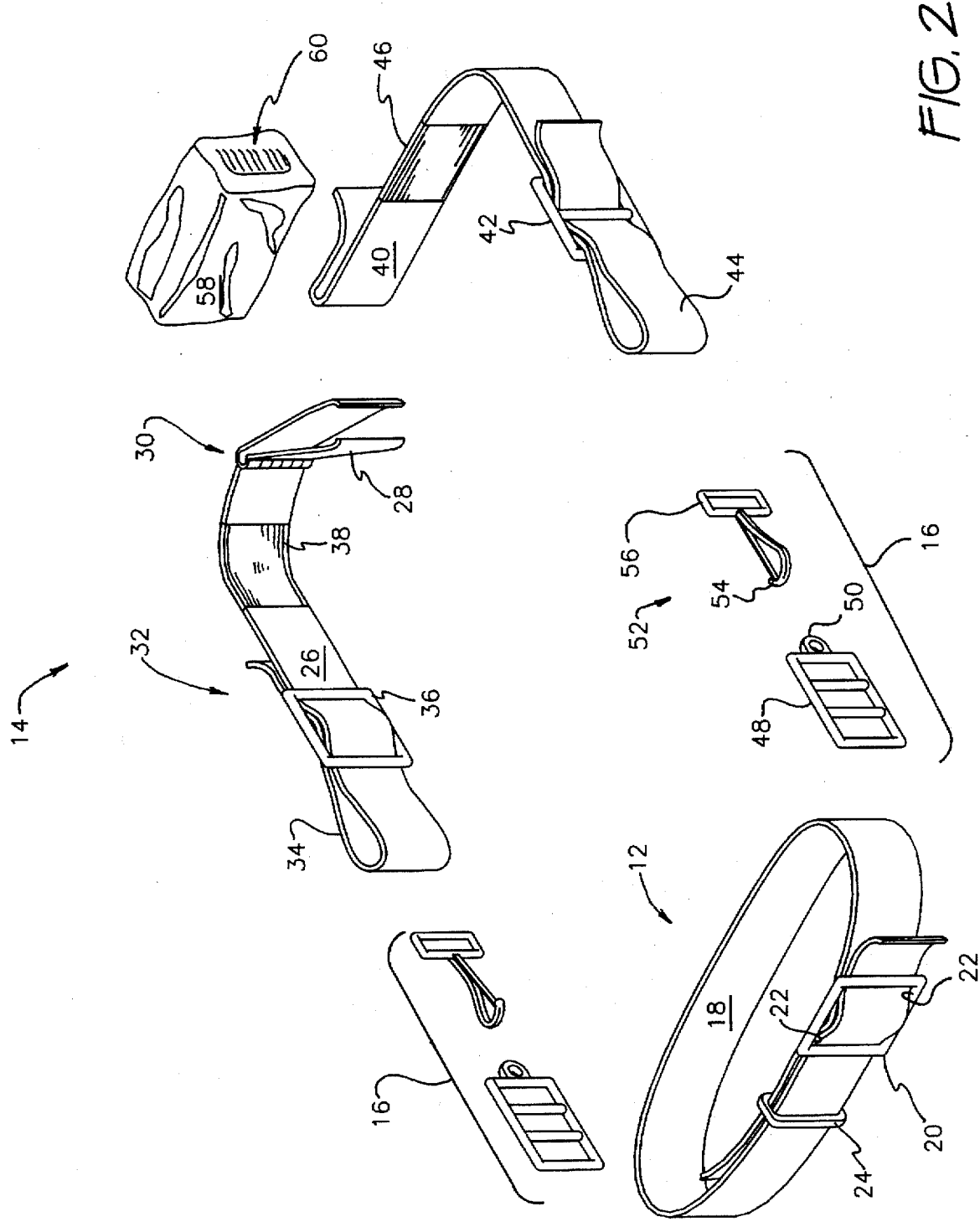
FIG. 2 is a perspective, partially exploded view of the invention.

Turning now to FIG. 2, harness 10 comprises, firstly, an anchoring member 12 for engaging seatback 4 by tight encirclement thereof, secondly, a support member 14 supporting the seated person P in an erect posture, and thirdly, attachment apparatus 16 for attaching support member 14 to anchoring member 12. Anchoring member 12 includes a continuous and imperforate flexible strap 18 and a sliding clip 20. Sliding clip 20 has two slots 22 formed therein, for accepting passage and enabling frictional retention of strap 18. A closed loop clip 24 may be provided for controlling excess length of strap 18 by encircling the overlapping sections of strap 18.

Support member 14 comprises a continuous and imperforate second flexible strap 26 having a suitable buckle, such as cam buckle 28, attached to its distal end 30. For clarity, strap 26 will be understood to have a proximal end section 32 which is folded over and fastened to form a loop 34 for attaching to anchoring member 12, and distal end 30.

Loop 34 is maintained as a loop by a sliding clip 36, which is essentially similar to sliding clip 20. Excess length of strap 26 hangs freely to the outside of strap 26. Should excess length of strap 26 become so great as to require retention, a clip similar to clip 20 may be employed.

Strap 26 has a section 38 of resilient, elastic material inserted serially therein. Elastic section 38 resiliently yields when subjected to a stretching force, such as inclination of the torso by the person seated in the chair.

Strap 26 is complemented by a third strap 40 which also is continuous and imperforate. Strap 40 is essentially a mirror image of strap 26, except that strap 40 requires no buckle. Strap 40 has a sliding clip 42 essentially similar to clip 36, for forming a loop 44 in strap 40. Strap 40 also includes an elastic and resilient section 46, so that elastic yielding will be symmetrical with respect to right and left sides of the user's torso. Of course, if desired, either section 38 or section 46 could be omitted, the function of elastic yielding being provided by only one section 38 or 46.

When installed on seatback 4 (see FIG. 1), anchoring member 12 is a closed loop having a circumference. Straps 26 and 40 each attach to anchoring member 12 at opposite lateral sides of anchoring member 26. Strap 26 attaches to the circumference of anchoring member at a point thereal-ong which is preferably midway between the front and the back of anchoring strap 12.

Preferably, attachment apparatus 16 comprises a pair of mating, separable members. One member 48 of the pair terminates in a sliding clip for engaging strap 18, and incorporates a ring 50 projecting from the sliding clip. The other member 52 is a snap hook 54 engageable with ring 50, snap hook 54 joined to a loop 56 for engaging strap 40. Locations of ring 50 and corresponding snap hook 54 may be reversed if desired.

Attachment apparatus 16 for connecting strap 40 to anchoring member 12 has thus been described. A similar attachment apparatus 16, but a mirror image thereof, is provided for connecting strap 26 to anchoring member 12. Member 48 of each attachment apparatus 16 is slipped over strap 18 of anchoring member 12 at a point on the circumference preferably diametrically opposed from a corresponding second point of attachment of the other member 48. The three slots 49 formed in member 48 will be seen to immobilize the attachment point of its associated strap 26 or 40, in the sense of preventing the attachment point from wandering from a selected point on the circumference of anchoring member 12. Also, ring 50 is held in a forwardly projecting orientation by immobilization of member 48, so that engagement by snap hook 54 is easily accomplished even when these components are out of direct line of sight. This result is obtained when strap 18 is passed through all three slots 49 of member 48.

The nature of attachment apparatus enables separable attachment of straps 26 and 40 to different points along the circumference of strap 18 of anchoring member 12, and also enables nearly universal flexure of each strap 26 or 40 with respect to strap 18. This arrangement enables straps 26 and 40 to accommodate bodily movement by the user, to be located midway between front and rear of anchoring member 12, and to meet and be mutually connected by buckle 28, thereby encircling the torso of the person seated in the chair.

A cover 58 is provided for cushioning contact of buckle 28 with the torso of the person seated in the chair. Cover 58 comprises a cushioned or padded sleeve having an opening 60 extending entirely through cover 58. Cover 58 may thus be slipped over strap 26 or strap 40 prior to buckling straps 26 and 40 together. Cover 58 is maneuvered over buckle 28 after straps 26 and 40 are mutually connected.

Thus it is seen that a precise combination of characteristics is created by cooperation among the components described above. This precise combination of characteristics leads to a posture maintaining harness which is both effective and easily connected to a chair and donned. Adjustments to assure symmetry of location of components and forces lead to avoidance of subconscious distraction of the user.

It is to be understood that the present invention is not limited to the embodiments described above, but encompasses any and all embodiments within the scope of the following claims.

I claim:

1. A harness for maintaining a person seated in a chair in an erect posture, said harness comprising:

an anchoring member comprising a continuous and imperforate first flexible strap and a first sliding clip having means defining at least two slots formed in said sliding clip for accepting passage of said first flexible strap and enabling frictional retention of said first flexible strap, said first flexible strap forming a closed loop having a circumference when an end of said first flexible strap is passed through said first sliding clip;

a support member comprising a continuous and imperforate second flexible strap having a proximal end and and a distal end, a buckle attached to said second flexible strap at said distal end thereof, and a second sliding clip having means defining at least two slots formed in said second sliding clip for accepting passage of said second flexible strap and enabling frictional retention of said second flexible strap, said second flexible strap forming a closed loop for engaging said anchoring member, said closed loop of said second flexible strap formed at said distal end of said second flexible strap by passing said second flexible strap through said second sliding clip, and a continuous and imperforate third flexible strap, and a third sliding clip having a proximal end and a distal end, means defining at least two slots formed in said third sliding clip for accepting passage of said third flexible strap and enabling frictional retention of said third flexible strap, said third flexible strap having a closed loop for engaging said anchoring member formed at said distal end of said third flexible strap by passing said distal end of said third flexible strap through said third sliding clip; and attachment apparatus for attaching said second flexible strap to said anchoring member at a point along said circumference of said anchoring member and for attaching said third flexible strap to said anchoring member at a second point along said circumference of said anchoring member, said first point along said circumference and said second point along said circumference being different points, said attachment means comprising two pairs of mating, separable members, one member of each pair of mating, separable member terminating in a sliding clip for engaging said first flexible strap of said anchoring member and the other member of each pair of mating, separable members terminating in a loop for engaging one of said second flexible strap and said third flexible strap, whereby said anchoring member may be fastened around the back of a chair, said second flexible strap being separably attachable to said anchoring member at a point along said circumference of said anchoring member by said attachment apparatus, and said third flexible strap being separably attachable to said anchoring member at a different point along said circumference of said anchoring member, and said second flexible strap and said third flexible strap being mutually connectable by said buckle, thereby encircling the torso of the person seated in the chair.

2. The harness according to claim 1, at least one of said second flexible strap and said third flexible strap having a section of resilient, elastic material inserted serially therein, whereby one of said second flexible strap and said third flexible strap resiliently yields when subjected to a stretching force.

3. The harness according to claim 1, further comprising a cover for covering said buckle means, said cover comprising a cushion for cushioning contact of said buckle means with the torso of the person seated in the chair.

4. The harness according to claim 1, said buckle means comprising a cam buckle.

5. The harness according to claim 1, at least one pair of said two pairs of mating, separable members comprising a ring projecting from one member of each pair of mating, separable members, and a snap hook joined to the other member of each pair of mating, separable members, said snap hook of one member engageable with said ring of the other member.

6. A harness for maintaining a person seated in a chair in an erect posture, said harness comprising:

an anchoring member comprising a continuous and imperforate first flexible strap and a first sliding clip having means defining at least two slots formed in said sliding clip for accepting passage of said first flexible strap and enabling frictional retention of said first flexible strap, said first flexible strap forming a closed loop having a circumference when an end of said first flexible strap is passed through said first sliding clip;

a support member comprising a continuous and imperforate second flexible strap having a proximal end and and a distal end, a buckle attached to said second flexible strap at said distal end thereof, and a second sliding clip having means defining at least two slots formed in said second sliding clip for accepting passage of said second flexible strap and enabling frictional retention of said second flexible strap, said second flexible strap forming a closed loop for engaging said anchoring member, said closed loop of said second flexible strap formed at said distal end of said second flexible strap by passing said second flexible strap through said second sliding clip, and a continuous and imperforate third flexible strap, and a third sliding clip having a proximal end and a distal end, means defining at least two slots formed in said third sliding clip for accepting passage of said third flexible strap and enabling frictional retention of said third flexible strap, said third flexible strap having a closed loop for engaging said anchoring member formed at said distal end of said third flexible strap by passing said distal end of said third flexible strap through said third sliding clip; and attachment apparatus for attaching said second flexible strap to said anchoring member at a point along said circumference of said anchoring member and for attaching said third flexible strap to said anchoring member at a second point along said circumference of said anchoring member, said first point along said circumference and said second point along said circumference being different points, said attachment means comprising two pairs of mating, separable members, one member of each pair of mating, separable members terminating in a sliding clip for engaging said first flexible strap of said anchoring member and the other member of each pair of mating, separable members terminating in a loop for engaging one of said second flexible strap and said third flexible strap, whereby said anchoring member may be fastened around the back of a chair, said second flexible strap being separably attachable to said anchoring member at a point along said circumference of said anchoring member by said attachment apparatus, and said third flexible strap being separably attachable to said anchoring member at a different point along said circumference of said anchoring member, and said second flexible strap and said third flexible strap being mutually connectable by said buckle, thereby encircling the torso of the person seated in the chair, at least one of said second flexible strap and said third flexible strap having a section of resilient, elastic material inserted serially therein, whereby one of said second flexible strap and said third flexible strap resiliently yields when subjected to a stretching force, said harness further comprising a cover for covering said buckle, said cover comprising a cushion for cushioning contact of said buckle with the torso of the person seated in the chair.

7. The harness according to claim 6, said buckle means comprising a cam buckle.

* * * * *